United States Patent [19]

Friend

[11] 4,011,868

[45] Mar. 15, 1977

[54] HYPODERMIC SYRINGE WITH ARTICULATE PLUNGER

[76] Inventor: John H. Friend, 10200 Arno Road, Galt, Calif. 95632

[22] Filed: May 19, 1975

[21] Appl. No.: 578,676

[52] U.S. Cl. .......................... 128/218 P; 128/234
[51] Int. Cl.² .......................................... A61M 5/00
[58] Field of Search .......... 128/218, 215, 216, 217, 128/219, 220, 221, 234, 224

[56] References Cited

UNITED STATES PATENTS

| | | | |
|---|---|---|---|
| 1,678,991 | 7/1928 | Marschalck | 128/218 PA |
| 2,390,246 | 12/1945 | Folkman | 128/215 |
| 3,495,591 | 2/1970 | Wilson | 128/218 R |

FOREIGN PATENTS OR APPLICATIONS

| | | | |
|---|---|---|---|
| 963,751 | 9/1953 | France | 128/218 N |
| 188,449 | 10/1906 | Germany | 128/234 |

*Primary Examiner*—John D. Yasko
*Attorney, Agent, or Firm*—John H. Crowe

[57] ABSTRACT

The plunger of a hypodermic syringe has the usual head and shank, but the shank is of articulate construction to permit change from a normal straight operating configuration to an angular configuration, at which angular configuration the shank engages the syringe barrel to control the position of the plunger head. In some embodiments the shank bends through an angle of 180° to lie along the exterior of the barrel and thereby straddle the rim of the barrel to cooperate therewith to limit movement of the plunger head inwardly of the barrel. The straddling folded shank may engage the barrel rim at selected points of the shank to immobilize the plunger head at selected positions. In other embodiments the articulate shank bends through only a small angle to cooperate with the barrel rim to control the plunger head.

15 Claims, 16 Drawing Figures

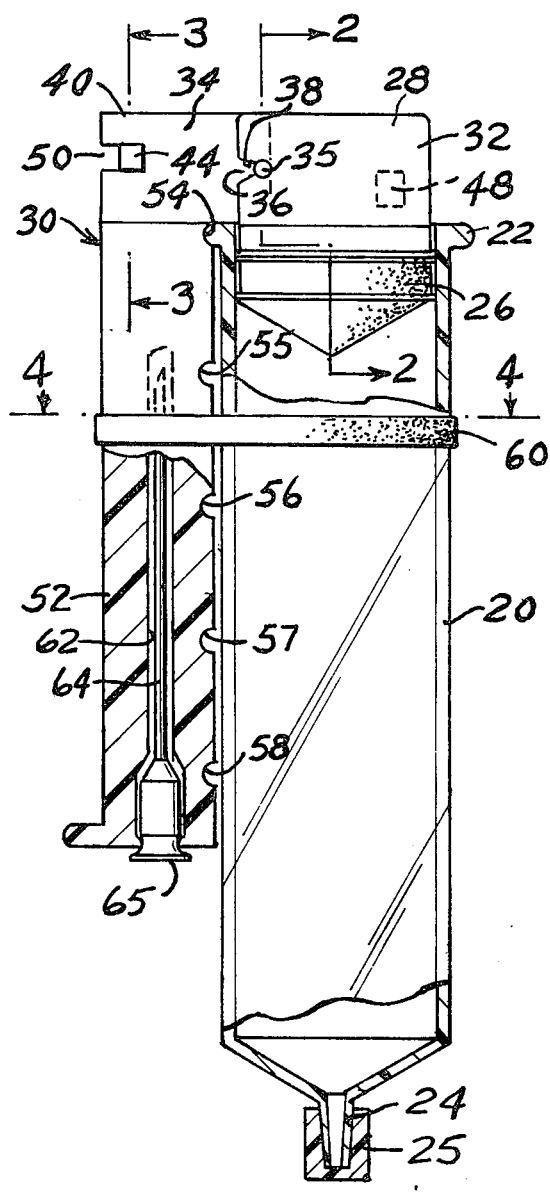
FIG. 1.
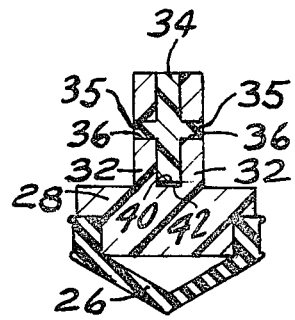
FIG. 2.
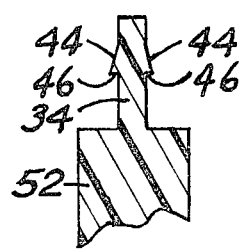
FIG. 3.
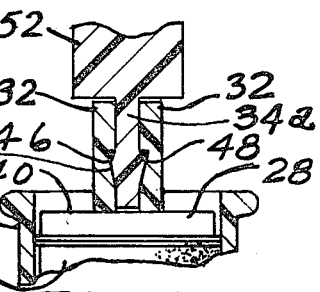
FIG. 6.
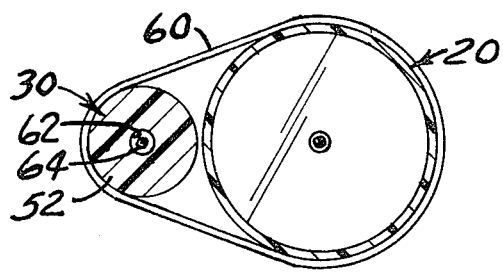
FIG. 4.
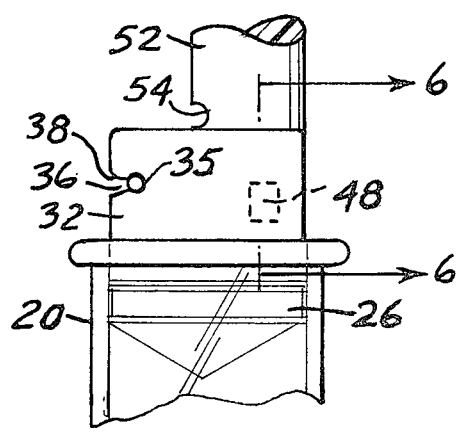
FIG. 7. FIG. 8.
FIG. 5.

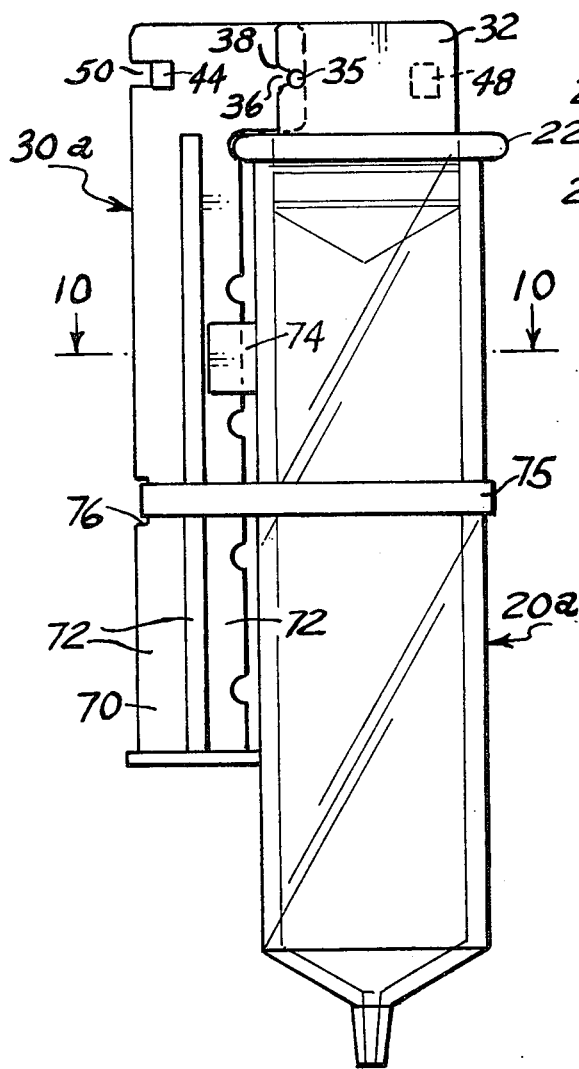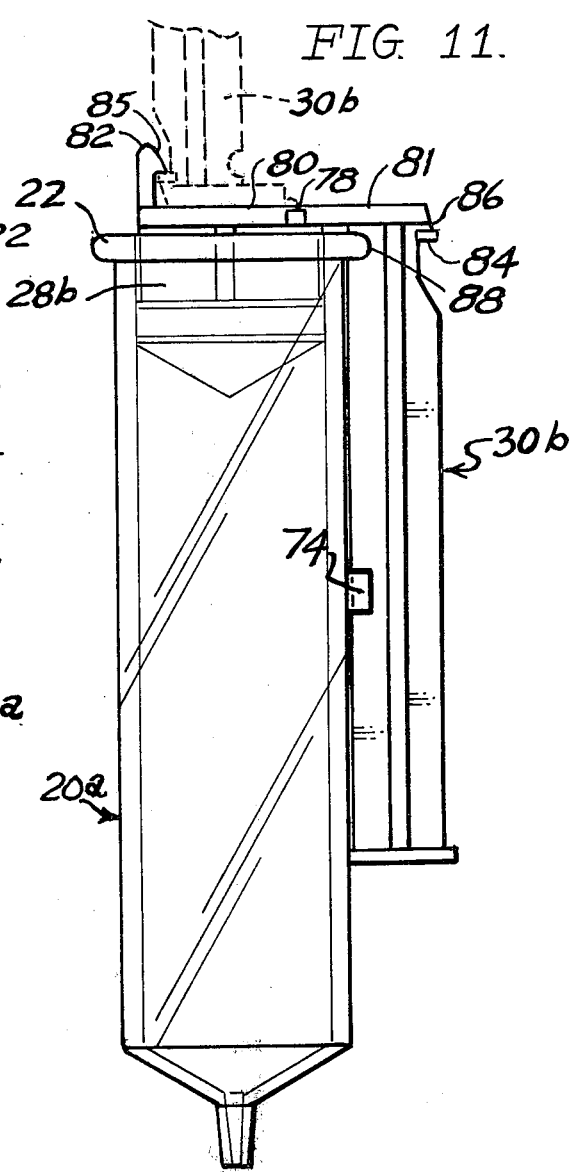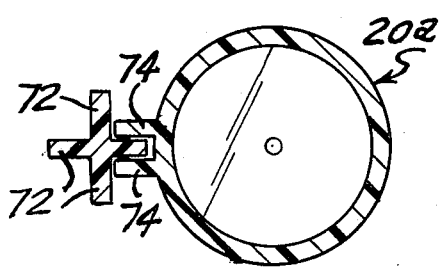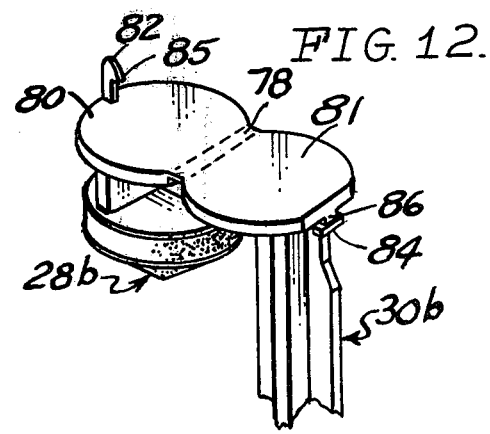

HYPODERMIC SYRINGE WITH ARTICULATE PLUNGER

BACKGROUND OF THE INVENTION

This invention relates to hypodermic syringes and is directed to the problem of controlling the position of a plunger head in a syringe barrel.

In many instances in medical practice, it is desirable to provide a hypodermic syringe with a liquid dosage of predetermined magnitude well in advance of the time of use. For example, a hypodermic syringe may be prefilled so that it may be instantly available in any emergency that may occur in an operating room or elsewhere. As another example, a nurse may provide a patient with several hypodermic syringes with premeasured doses for self-medication by the patient periodically over a period of time. An increasingly common example is the packaging of prefilled dispensable hypodermic syringes by pharmaceutical manufacturers for maximum convenience to medical personnel.

A serious problem in such practices arises from the fact that when a premeasured medication is placed in a conventional hypodermic syringe well in advance of the time of use, the syringe plunger is necessarily retracted to an exposed position extending well beyond the open end of the syringe barrel, and the exposed plunger may be accidentally or inadvertently advanced to some degree prior to the time of use. The consequence is wasteful loss of at least a portion of the medication and, unfortunately, the unintended reduction in the dosage may not be noticed. In a hospital or a nursing home, prefilled syringes may be kept handy in good supply for instant use, and under such circumstances leakage losses occur even with the greatest care by personnel.

In many instances, syringes are prefilled at a central point by a pharmacist and then transported in quantity to a hospital or nursing home, and the additional handling for transportation greatly increases the possibility of the syringes leaking prior to use.

A pharmaceutical manufacturer shipping prefilled syringes to points of use may take special precautions to guard the extended plungers against accidental forces. One expedient is to place each extended hypodermic syringe in an elongated package designed to afford some protection to the extended plunger. At the time of use, one end of the package is torn off for access to the syringe. Such packages are necessarily of inexpensive construction and therefore not strong enough to fully protect the extended syringes.

One solution to the problem employed by some pharmaceutical manufacturers is to place in one package a cartridge containing a predetermined quantity of medication and a separate specialized syringe barrel designed to receive the cartridge. Typically, the package contains a plastic tray with two elongated cavities therein to nest the cartridge and the specialized spring barrel, respectively. When the package is opened at the time of use, protective plastic caps on the cartridge and the barrel, respectively, must be removed and discarded. Then a retracted plunger head in the cartridge is screwed into engagement with the end of an inner tube in the specialized barrel to cause a long fixed axial needle in the inner tube to pierce the plunger head to place the cartridge medication in communication with the needle at the discharge end of the specialized barrel.

This solution to the problem has numerous disadvantages including: the additional cost of the special package; the additional cost of the separate cartridge; the additional cost of the protective caps for the cartridge and the barrel, respectively; and, finally, the additional cost of the inner tube and axial needle in the specialized barrel. Another disadvantage is that the package is bulky not only because it contains a cartridge as well as a specialized barrel, but also because the capacity of the barrel is in the inner tube, not the barrel proper, and therefore the syringe barrel is necessarily of enlarged diameter.

A further disadvantage is that the syringe is not instantly useable in an emergency. Delay is required by the various steps of opening the package, removing the cartridge and barrel, removing the plastic caps from the cartridge and the barrel, respectively, and then screwing the cartridge into the inner tube of the specialized barrel.

With further reference to the background of the invention, another problem arises that does not relate to prefilled syringes but rather relates to syringes which are filled with medication at the time of use. This problem is the tendency of the plunger of a hypodermic syringe to shift position in response to a fluid-pressure differential across the plunger head.

For example, if a hypodermic needle is inserted in a tubing line for intravenous treatment of a patient, and the plunger of the needle is to be advanced periodically for introducing successive predetermined quantities of medication, the fact that the fluid pressure in the tubing line is always above atmospheric pressure results in a pressure differential across the plunger of the hypodermic syringe that tends to cause the plunger to creep outwardly of the syringe barrel. Thus fluid from the intravenous line backs up into the hypodermic syringe to dilute the medication in the syringe, and there is no way of knowing how far the plunger should be advanced at the end of the next time period to introduce a new predetermined quantity of the medication.

Another example is the manual retraction of the plunger of a hypodermic syringe to create a vacuum in the syringe barrel for drawing fluid into the syringe from a vial or from a body cavity. In such an instance the vacuum tends to advance the plunger, and it is desirable to provide some means to eliminate the necessity for the user to hold the plunger in retracted position over a period of time to resist the effect of the vacuum.

SUMMARY OF THE INVENTION

The general object of the invention is to provide syringes that solve the numerous problems mentioned above.

Specific objects of the invention include: providing a prefilled hypodermic syringe that is exceedingly compact; providing a prefilled hypodermic syringe that may be sold and shipped in a simple, inexpensive paper container; providing a prefilled hypodermic syringe that prior to use is immune to leakage caused by accidental or inadvertent forces against the retracted syringe plunger; providing a hypodermic syringe which the purchaser may fill or partially fill with medication for future use and then have the syringe available over an indefinite period of time with the assurance that none of the medication will be lost by accidental movement of the syringe plunger; providing a prefilled hypodermic syringe, in which the head of the plunger may be releasably locked against movement until the time of use of the syringe; providing such a prefilled hypodermic syringe in which the head of the plunger may be immobilized at selected positions; providing a prefilled hypodermic syringe in which the plunger is locked against movement but which is instantly available for use in an emergency; providing such a prefilled hypodermic syringe that requires neither skill nor special knowledge to prepare the syringe for use; providing a prefilled hypodermic syringe of low cost that may be packaged for shipment at low cost; providing a hypodermic syringe that may be fabricated and assembled at low cost even though it has an additional movable part to immobilize the plunger; and providing such a prefilled hypodermic syringe that may be effectively sealed to prevent tampering prior to the time of use.

To meet these various objectives, the plunger of the syringe is provided with an articulate shank that may be bent from a normal straight operating configuration to an angular configuration to cooperate with the barrel to control the position of the plunger head.

One of two types of hypodermic syringe disclosed herein is intended primarily to serve as a syringe that may be filled in advance at some central point and then shipped and handled prior to use. It is highly desirable, first, that the plunger of the prefilled syringe be immune to accidental forces during shipment and handling prior to the time of use and, second, that the prefilled syringe be capable of contraction to a compact package for shipment and storage.

In this first type of syringe that is intended to be prefilled, the articulate shank of the syringe bends 180° from its normal straight operating configuration to an angular configuration at which the folded shank extends along the exterior of the barrel and straddles the rim of the barrel to cooperate with the barrel to control the position of the plunger head in the barrel. The folded shank may be provided with a plurality of latch elements spaced along the length of the shank to engage the syringe barrel selectively to control the plunger head at selected positions in the barrel.

The second of the two types of hypodermic syringe disclosed herein is not prefilled at some central point and therefore does not require protection during shipment. The articulate shank of this second type of syringe bends through only a small angle from the normal straight operating configuration of the shank to an angular configuration at which the shank engages the barrel of the syringe to resist a fluid-pressure differential across the head of the plunger. Here again, the shank of the plunger has a plurality of longitudinally spaced latch elements for selective engagement with the barrel to resist pressure differentials at selected positions of the plunger head in the barrel.

The invention is further characterized by the use of various latch means for various purposes. In the first type of syringe, for example, the shank of the plunger is automatically latched to the barrel when the shank is folded back against the exterior of the barrel. The invention also teaches that another type of latch may be incorporated in the articulate plunger shank itself to releasably maintain the plunger shank at its normal straight operating configuration, the latch engaging automatically in response to return of the shank from its angular configuration to its normal straight configuration.

In some embodiments of the invention, the cost of the syringe is kept low by making the shank of the syringe in two separate molded plastic parts that may be simply snapped together at the pivotal connection of the two parts. In another embodiment of the invention even greater reduction in the cost of fabrication is achieved by molding two plastic sections of an articulate shank in one piece with the two sections interconnected by a flexible hinge portion that is integral with both sections.

A further object of one embodiment of the invention is to provide a prefilled hypodermic syringe that is reduced in overall length not only by the folding of the plunger shank, but also by storing the needle of the syringe in the shank. The outlet of the prefilled syringe barrel is releasably capped for shipment. To ready the prefilled syringe for use, the cap is removed and is replaced by the needle which is withdrawn from its stored position in the shank of the plunger.

The various features and advantages of the invention may be understood from the following detailed description and the accompanying drawings.

BRIEF DESCRIPTION OF THE DRAWING

In the drawings, which are to be regarded as merely illustrative;

FIG. 1 is a side elevational view, partly in section, of an embodiment of the first type of hypodermic syringe that is designed for prefilled use;

FIG. 2 is a fragmentary section along the line 2—2 of FIG. 1 showing the construction of a snap-on pivotal connection between the two sections of the articulate shank of the plunger;

FIG. 3 is a fragmentary section along the line 3—3 of FIG. 1;

FIG. 4 is a transverse section along the line 4—4 of FIG. 1;

FIG. 5 is a view similar to FIG. 1 showing the shank of the plunger at its normal straight operating configuration;

FIG. 6 is a fragmentary section along line 6—6 of FIG. 5 showing the means incorporated in the articulate shank to releasably maintain the shank at its normal straight operating position;

FIGS. 7 and 8 are fragmentary sectional views similar to FIG. 2 showing an alternative construction for the snap-on pivotal connection between the two shank sections;

FIG. 9 is a side elevational view similar to FIG. 1 illustrating a second embodiment of the first type of hypodermic syringe;

FIG. 10 is a transverse section along the line 10—10 of FIG. 9 showing the construction of a friction latch for the folded plunger shank;

FIG. 11 is a side elevational view of a third embodiment of the first type of hypodermic syringe showing the shank of the plunger in its folded configuration;

FIG. 12 is an enlarged fragmentary perspective view of the folded shank shown in FIG. 11;

FIG. 14-A is a fragmentary view similar to FIG. 14 showing an alternative latch arrangement;

DESCRIPTION OF THE SELECTED EMBODIMENTS OF THE INVENTION

Figure 13:
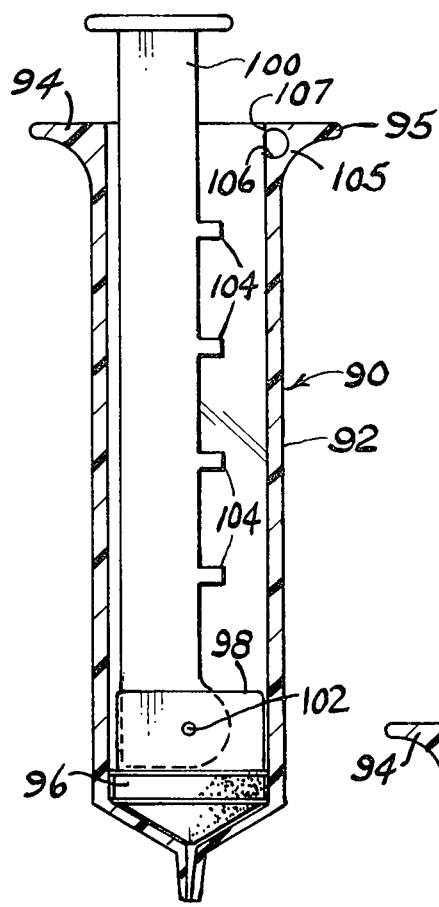
FIG. 13 is a side elevational view, partly in section, of an embodiment of the second type of hypodermic syringe that is not intended for prefilled use, the plunger being shown at its fully advanced position.

The barrel 20 of the first embodiment of the invention, shown in FIGS. 1-6, is made of clear glass or plastic material with the usual rim flange 22 at its open end and with a reduced neck 24 at its outlet end. The reduced neck is normally closed by a removable cap 25 to prevent leakage of the liquid medication from the barrel. The plunger of the syringe has a conventional head 26 that fits slidably in the barrel, and the shank of the plunger is divided into two pivotally connected sections comprising an inner section 28 that is united with the plunger head 26 and an outer section 30 that is foldable against the exterior of the barrel in the manner shown in FIG. 1.

The inner section 28 of the shank that is unitary with the plunger head 26 is formed with two slightly flexible parallel blades 32, and the outer section 30 of the foldable shank has a blade portion 34 that fits in a slidable manner between the two blades 32. The blade portion 34 of the outer shank section 30 is formed with a pair of opposite trunnions 35 that are journaled in corresponding recesses 36 in the two blades 32. The two recesses 36 are in the form of slots which are of tapered configuration as shown and are formed with lips 38 to retain the trunnions 35. To pivotally connect the two shank sections merely requires that the two trunnions 36 be forced into the two slots until the trunnions snap into place behind the lips 38.

It can be seen in FIG. 1 that the outer section 30 of the shank of the plunger is of angular configuration that provides what may be termed a "heel" surface 40. When the two-section shank is unfolded, as shown in FIGS. 5 and 6, the heel surface 40 of the blade 34 abuts a corresponding end surface 42 of the inner shank section. Thus when the shank is unfolded, as shown in FIG. 5, and manual force is applied to the outer shank section 30 to advance the plunger head 26 in the barrel 20, the operating force is transmitted to the plunger head 26 by mutual abutment of the heel surface 40 and the end surface 42, the operating force largely, if not entirely, bypassing the two trunnions 35. Since the two trunnions 35 are not subjected to much, if any, of the operating force, the only load imposed on the trunnions is the load that is incidental to the folding and unfolding of the plunger shank.

The design of a latch to hold the shank in its unfolded operating configuration takes advantage of the fact that the two blades 32 of the inner shank section 28 are made of plastic material and therefore are flexible to a certain degree. The latch includes two opposite latch elements 44 that are integral with the blade portion 34, as shown in FIGS. 1 and 3. Each of the two latch elements 44 has a gradually sloped leading shoulder and an abrupt trailing shoulder 46. As shown in section in FIG. 6, the two blades 32 of the inner shank section 28 are formed with latching recesses 48 of the same configuration as the latch elements 44.

When the shank of the plunger is unfolded to the operating configuration shown in FIG. 5, the two latch elements 44 of the blade portion 34 of the outer shank section move into the space between the two blades 32 with wedging action that flexes the two blades and then the latch elements 44 snap into engagement with the latching recesses 48, as may be seen in FIG. 6.

Since the syringe is usually intended to be a disposable syringe that is to be discarded after a single use, there is usually no need to release the described latch to permit the plunger shank to be returned to its folded position. If, however, it is desired to unlatch the unfolded plunger shank, the two blades 32 may be flexed away from each other by a suitable tool, such as a screwdriver. To facilitate such an operation, the blade portion 34 of the outer shank section 30 may be provided with a recess 50 (FIG. 1) adjacent the two latch elements 44 to admit the end of a screwdriver.

The outer shank section 30, which is made of suitable plastic material, has an elongated body 52 which is of circular cross-section, as may be seen in FIG. 4, and which is integral with the blade portion 34. When the plunger shank is in its folded configuration, shown in FIG. 1, it can be seen that the folded shank straddles the rim of the open end of the barrel 20 to limit the degree to which the plunger head 26 may be advanced in the barrel by any accidental force that may be applied to the folded shank. At the folded position of the shank, a latch element in the form of a recess 54 in the outer section 30 of the shank engages the rim flange 22 not only to prevent advance movement of the plunger head 26 in the barrel, but also to prevent retraction movement of the plunger head. In this embodiment of the invention, the outer shank section 30 has four additional spaced recesses 55–58 to engage the rim flange 22 of the syringe barrel selectively to immobilize the plunger head 26 at selected positions in the syringe barrel 20.

Preferably, suitable means is provided to releasably retain the plunger shank in its folded state until the time of use of the syringe. In this first embodiment of the invention, a removable rubber band 60 embraces both the barrel 20 and the outer shank section 30 for this purpose. It is to be noted that the rubber band 60 urges the outer shank section 30 toward its folded position and thus permits the folded shank section to serve as a clip for releasably engaging a breast pocket of a garment.

The body 52 of the outer section 30 of the foldable shank has a blind bore 62 that is open to the outer end of the shank to serve as a well in which the needle 64 of the hypodermic syringe may be stored until the time of use. The needle 64 is of conventional construction and has an enlarged base 65 to embrace the reduced neck 24 of the syringe barrel 20. As shown in FIG. 1, the enlarged base 65 of the needle protrudes from the outer end of the blind bore 62 to facilitate manual withdrawal of the needle from the bore. At the time of use of the syringe, the cap 25 is removed and is replaced by the needle 64. It is apparent that the syringe may be quickly prepared for use since it is necessary merely to remove the rubber band 60 and to substitute the needle 64 for the cap 25.

FIGS. 7 and 8 are sectional views similar to FIG. 6 showing an alternative construction that may be employed to permit assembly of the outer shank section 30 to the inner shank section 28 by snap action. In this alternative structure, the two blades 32a of the inner shank section 28 are provided with simple bores 66 instead of the previously described slots 36. The blade portion 34a of the outer section of the shank is formed with a pair of opposite trunnions 68 which are of conical cross-section, as best shown in FIG. 7. In assembling the outer shank section to the inner shank section, the blade portion 34a of the outer shank section is first positioned as shown in FIG. 7 and then the blade portion 34a is forced to the assembled position shown in FIG. 8. The two conical trunnions 68 wedge between the two blades 32a to flex the two blades away from each other until the two trunnions snap into engagement with the two bores 66.

The second embodiment of the invention shown in FIGS. 9 and 10 is similar to the first embodiment, as indicated by the use of corresponding numerals to indicate corresponding parts. Instead of the outer shank section 30a having a body of circular cross-section, the body 70 shown in FIG. 9 is of cruciform cross-section with four longitudinal flanges or ribs 72. Instead of applying a rubber band to releasably retain the shank in its folded state, the plastic barrel 20a of the syringe is formed with a pair of parallel ears 74 that are dimensioned for frictional engagement with the inner flange 72 of the shank body 70. When the outer shank section 30a is swung to its fully folded position, the innermost flange 72 of the outer shank section 30a is forced between the two ears 74 into effective frictional engagement with the two ears.

When the hypodermic syringe shown in FIG. 9 is prefilled with medication and the shank of the syringe plunger is folded as shown in FIG. 9, a frangible band 75 may be added to embrace the barrel 20a and the body 70 of the plunger shank, the band seating in a notch 76 in the folded shank. The band 75 may be made of heat-shrinkable plastic and serves as a seal to indicate whether or not anyone has tampered with the prefilled syringe prior to the time of use. The notch 76 in the body 70 of the folded shank prevents removal of the shrunk band 75 without rupture of the band.

The hypodermic syringe shown in FIGS. 11 and 12 is similar in general to the embodiment shown in FIG. 9, as indicated by the corresponding reference numerals. The foldable shank of the syringe plunger is divided into an inner section 28b and an outer section 30b which are interconnected by a flexible hinge portion 78 that is integral with both sections. The two shank sections are of cruciform cross-sectional configuration as shown, the inner section 28b having an inner end wall 80 and the outer section 30b having a similar end wall 81 with the two end walls interconnected by the flexible hinge portion 78. It is apparent that the foldable shank of the plunger of the syringe may be molded in one piece.

It is contemplated that when the outer shank section 30b is swung from its folded position shown in FIG. 12 to its upright operating position shown in dotted lines in FIG. 11, the two shank sections will be automatically latched together. For this purpose, the end wall 80 of the inner shank section 28b is formed with a latch hook 82 and the end wall 81 of the outer shank section 30b is formed with a cooperative latch member 84 for releasable engagement by the latch hook. The latch hook 82 has an inclined surface 85 and the latch member 84 has a cooperating inclined surface 86. When the outer shank section 30b is swung to its operating position that is indicated by dotted lines in FIG. 11, the two inclined surfaces 85 and 86 meet and slide along each other with cam action until the latch member 84 snaps into engagement with the latch hook 82. The operating force applied to the outer end of the unfolded plunger shank is transmitted from the end wall 81 to the end wall 80.

Preferably the flexible hinge 78 is biased to urge the shank to its folded configuration. This bias enables the folded shank to serve as a clip to engage the breast pocket of a garment.

The outer shank section 30b is formed with a latch element in the form of a recess 88 that engages the rim flange 22 of the syringe barrel when the outer section of the shank is folded against the barrel, as shown in FIG. 11. Thus the folded shank of the plunger cooperates with the rim flange 22 to immobilize the plunger of the syringe against both inward or outward displacement. The barrel 20a of the syringe is identical with the barrel 20a of the embodiment shown in FIG. 9, the barrel being formed with the previously described pair of flexible ears 74 for frictional engagement with a longitudinal flange of the outer shank section in the manner heretofore described.

FIGS. 13–16 illustrate embodiments of the second type of hypodermic syringe that is not intended for prefilled use. This type of syringe is intended primarily to resist a fluid-pressure differential across the plunger head of the syringe.

Figure 14A:
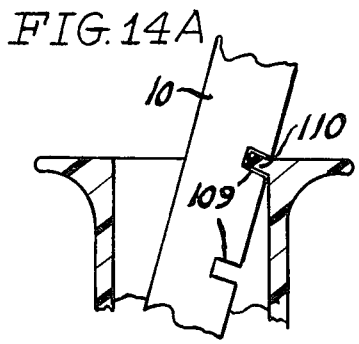
FIG. 14 is a similar view with the plunger retracted and bent through a small angle into engagement with the barrel to resist a fluid-pressure differential across the plunger head.
Figure 14:
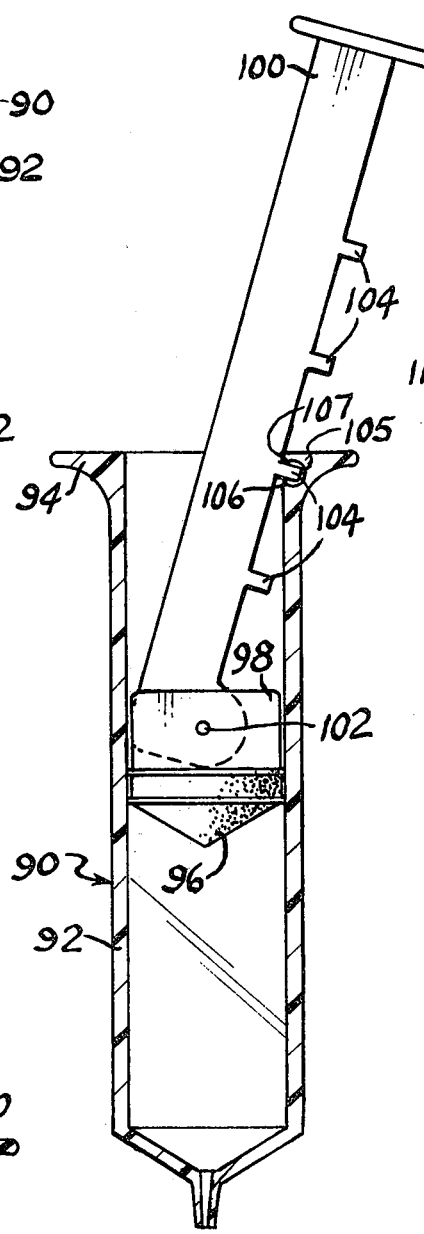

Referring first to FIGS. 13 and 14, the syringe, generally designated by the numeral 90, has a barrel 92 with two diametrically opposite enlargements 94 and 95 of the barrel rim, which enlargements serve as finger pieces when the outer end of the plunger shank is depressed by thumb pressure to advance the plunger head in the barrel. The syringe has the usual plunger head 96, which is controlled by an articulate shank, an inner section 98 of the shank being unitary with the plunger head and an outer section 100 being connected to the inner section by a pivot 102. In the manner heretofore described relative to the first two embodiments of the invention, the inner section 98 of the articulate shank comprises two parallel blades, which confine the blade-like inner end of the outer section 100.

It is contemplated that the outer section 100 of the articulate shank will be provided with longitudinally spaced latch elements for selective engagement with a complementary latch element on the barrel in the region of the rim of the barrel. The spaced latch elements on the shank section 100 may be either in the form of recesses or teeth, but in this instance the spaced latch elements on the shank section 100 are in the form of spaced teeth 104, and the cooperating latch element on the barrel 90 is in the form of a recess 105 in the rim enlargement 95, the recess being shaped and dimensioned for releasable engagement by the teeth.

In the construction shown, recess 105 has two confronting rounded overhanging shoulders 106 and 107 to releasably confine the teeth 104 selectively, the teeth making tangential abutment with the rounded shoulders. The spacing between the successive teeth 104 corresponds to dosage increments of predetermined magnitude, for example, increments of 5 or 10 cubic centimeters of the medication.

FIG. 14 shows the articulate shank bent through a relatively small angle for engagement of a selected tooth 104 of the shank with rounded shoulders of the recess 105. If a fluid differential across the plunger head 96 tends to retract the plunger head, the rear shoulder of the selected tooth 104 backs tangentially against the forwardly directed rounded shoulder 107 of recess 105 to prevent outward creepage of the plunger head. On the other hand, if the pressure differential across the plunger head tends to advance the plunger head in the barrel 92, the front shoulder of the selected tooth 104 tangentially abuts the rearwardly directed rounded shoulder 106 of recess 105 to prevent inward creepage of the plunger head.

It is apparent that FIGS. 13 and 14 actually embody two different forms of the invention, one form for latch action to resist fluid pressure that urges the plunger outwardly and a form for latch action to resist fluid pressure that urges the plunger inwardly. Each of the two forms could be embodies separately, but combining the two forms results in a single hypodermic syringe for universal utility.

If the plunger head 96 is retracted as shown in FIG. 14 for the purpose of creating a vacuum in the barrel to draw fluid into the barrel, the plunger shank may be latched to the barrel as shown to relieve the user of the burden of manually maintaining the plunger head retracted in opposition to the vacuum in the barrel. On the other hand, if the plunger head 96 is periodically advanced for the periodic discharge of the confined medication, the plunger shank may be latched at each of successive positions to hold each position in opposition to fluid pressure in the barrel that tends to drive the plunger head outward.

FIG. 14-A indicates how the latch elements on a shank section 100a may be in the form of spaced recesses 109 for selective, releasable engagement with a single tooth or projection 110 on the rim of the syringe barrel.

Figure 16:
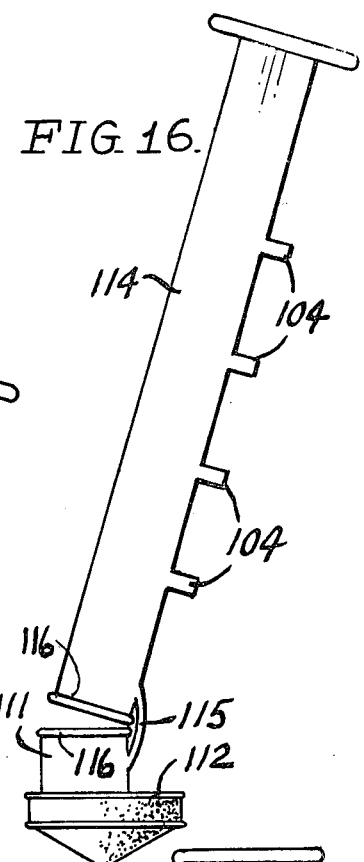
FIG. 16 is a view similar to FIG. 15 showing the articulate plunger in an angular configuration for cooperation with the barrel in the manner shown in FIG. 14.
Figure 15:
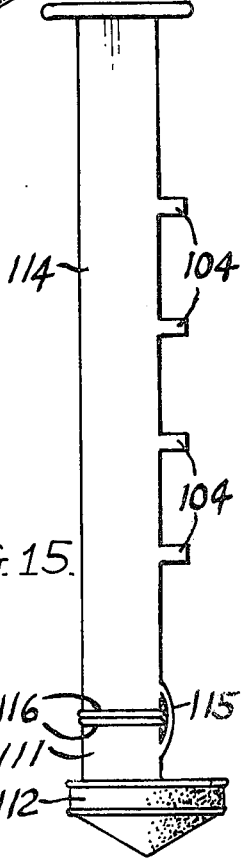
FIG. 15 is a side elevational view of an articulate plunger that may be substituted for the articulate plunger in FIGS. 13 and 14, the plunger being shown in its normal straight operating configuration.

FIGS. 15 and 16 illustrate an articulate plunger construction that may be substituted for the articulate plunger construction shown in FIGS. 13 and 14. The articulate shank shown in FIGS. 15 and 16 has an inner section 111 that is unitary with a plunger head 112 and has an outer section 114 that is connected to the inner section by a flexible hinge 115. The flexible hinge 115 is integral with both of the shank sections 111 and 114 to permit the two shank sections to be molded as a single piece of plastic. The confronting ends of the two shank sections 111 and 114 are preferably formed with heads 116, respectively, which as shown in FIG. 15 abut each other at the straight operating configuration of the articulate shank for the transmission of operating force from the outer shank section 114 to the inner shank section 111. The outer shank section 114 is provided with previously described spaced teeth 104 for selective engagement with the recess 105 of the syringe barrel 92.

A feature of this embodiment of the invention is that the flexible hinge 115 is biased to urge the outer shank section 114 toward the rim of the barrel. Thus the flexible hinge 115 functions as a leaf spring to keep a tooth 104 of the shank in engagement with the recess 105 in the rim of the barrel.

My description in specific detail of the selected embodiments of the invention will suggest various changes, substitutions and other departures from my disclosure within the spirit and scope of the appended claims.

I claim:

1. In a hypodermic syringe, the combination of:
a barrel open at one end and having a discharge port at the other end;
a plunger head slidingly mounted in the barrel to discharge the contents of the barrel through the discharge port; and
a shank connected to the plunger head;
said shank being foldable from an operating configuration aligned with the plunger head to an angular configuration to cooperate with the barrel to limit movement of the plunger in at least one direction relative to the barrel;
said combination including cooperative means on the shank and barrel, respectively, to releasably engage each other at the angular configuration of the shank to immobilize the plunger head in the barrel.

2. A combination as set forth in claim 1 in which the two cooperative means are shaped and dimensioned to frictionally engage each other at the angular configuration of the shank.

3. In a hypodermic syringe, the combination of:
a barrel open at one end and having a discharge port at the other end;
a plunger head slidingly mounted in the barrel to discharge the contents of the barrel through the discharge port; and
a shank connected to the plunger head,
said shank being foldable from an operating configuration aligned with the plunger head to an angular configuration to cooperate with the barrel to limit movement of the plunger in at least one direction relative to the barrel,
said combination including cooperative means on the barrel and the shank, respectively, at the angular configuration of the shank to releasably engage each other at a plurality of positions of the plunger head to selectively immobilize the plunger head.

4. A combination as set forth in claim 3 in which the shank has a plurality of spaced elements for selective engagement with the rim region of the barrel at the angular configuration of the shank.

5. In a hypodermic syringe, the combination of:
a barrel open at one end and having a discharge port at the other end;
a plunger head slidingly mounted in the barrel to discharge the contents of the barrel through the discharge port; and
a shank connected to the plunger head,
said shank being foldable from an operating configuration aligned with the plunger head to an angular configuration cooperate with the barrel to limit movement of the plunger in at least one direction relative to the barrel,
said shank being made in two sections interconnected by a flexible hinge that is integral with both sections, and
the confronting ends of the two sections abutting each other at the operating configuration of the shank for translation from section to section of operating force applied to the shank.

6. A combination as set forth in claim 5 which includes cooperative means on the inner ends of the two sections to releasably engage each other to maintain the shank at its operating configuration.

7. In a hypodermic syringe, the combination of:
a barrel open at one end and having a discharge port at the other end;
a plunger head slidingly mounted in the barrel to discharge the contents of the barrel through the discharge port; and
a shank connected to the plunger head,
said shank being foldable from an operating configuration aligned with the plunger head to an angular configuration to cooperate with the barrel to limit movement of the plunger in at least one direction relative to the barrel, said shank having a plurality of latch elements spaced longitudinally thereof to selectively and releasably engage the barrel of the syringe in the rim region thereof at the angular configuration of the shank.

8. A combination as set forth in claim 7 in which said latch elements have rearwardly facing shoulders and the barrel has a forwardly facing shoulder for releasable engagement by the rearwardly facing shoulders to prevent retraction of the plunger head by fluid-pressure differential across the plunger head.

9. A combination as set forth in claim 7 in which said latch elements have forwardly facing shoulders and the barrel has a rearwardly facing shoulder for releasable engagement by the forwardly facing shoulders to prevent advance of the plunger head by fluid-pressure differential across the plunger head.

10. A combination as set forth in claim 7 in which each of said spaced latch elements comprises a tooth forming a pair of oppositely facing shoulders and the barrel has a pair of confronting shoulders to releasably confine said oppositely facing shoulders to immobilize the plunger at selected positions in the syringe barrel.

11. A combination as set forth in claim 10 in which the pair of confronting shoulders of the barrel are rounded for tangential contact with said spaced latch elements.

12. A combination as set forth in claim 7 in which said spaced latch elements on the shank are in the form of recesses and the barrel is formed with a projection to engage the recesses selectively to immobilize the plunger at selected positions in the syringe barrel.

13. In a hypodermic syringe, the combination of:
a barrel open at one end and having a discharge port at the other end;
a plunger head slidingly mounted in the barrel to discharge the contents of the barrel through the discharge port; and
a shank connected to the plunger head,
said shank being foldable from an operating configuration aligned with the plunger head to an angular configuration to cooperate with the barrel to limit movement of the plunger in at least one direction relative to the barrel and being made in two sections comprising an inner section attached to the plunger and an outer section that is hingedly connected to the inner section,
the inner ends of the two sections being formed with respective surfaces that abut when the shank is in its operating configuration, thereby to cause at least a part of the operating force to bypass the hinge connection between the two shank sections.

14. In a hypodermic syringe, the combination of:
a barrel open at one end and having a discharge port at the other end;
a plunger head slidingly mounted in the barrel to discharge the contents of the barrel through the discharge port; and
a shank connected to the plunger head,
said shank being foldable from an operating configuration aligned with the plunger head to an angular configuration to cooperate with the barrel to limit movement of the plunger in at least one direction relative to the barrel and being made in two sections comprising an inner section attached to the plunger head and an outer section that is hingedly connected to the inner section,
one of the two sections having an integral pivot portion and the other of the two sections being recessed for cooperation with the pivot portion and being resiliently yieldable to receive the pivot portion by snap action in the assembly of the shank.

15. In a hypodermic syringe, the combination of:
a barrel open at one end and having a discharge port at the other end;
a plunger head slidingly mounted in the barrel to discharge the contents of the barrel through the discharge port; and
a shank connected to the plunger head,
said shank being foldable from an operating configuration aligned with the plunger head to an angular configuration to cooperate with the barrel to limit movement of the plunger in at least one direction relative to the barrel,
said combination including a needle for the barrel and said shank providing storage space for the needle,
said needle having an enlarged base end, and the outer end of the shank having a longitudinally extending bore to receive the needle, said enlarged base end of the needle being larger than the end of the bore for protrusion from the bore to facilitate removal of the needle from the bore.

* * * * *